United States Patent [19]

Hall et al.

[11] Patent Number: 4,740,504
[45] Date of Patent: Apr. 26, 1988

[54] ANTIHYPERLIPIDEMIC AMINE BORANES

[75] Inventors: Iris H. Hall, Chapel Hill, N.C.; Robert J. Brotherton, Laguna Beach; Edward L. Docks, Santa Ana, both of Calif.

[73] Assignee: United States Borax & Chemical Corp., Los Angeles, Calif.

[21] Appl. No.: 11,178

[22] Filed: Feb. 5, 1987

Related U.S. Application Data

[63] Continuation-in-part of Ser. No. 785,641, Oct. 8, 1985, abandoned.

[51] Int. Cl.$^4$ ............................................. A61K 31/69
[52] U.S. Cl. ................................................... 514/64
[58] Field of Search .................. 568/1; 514/64; 546/13

[56] References Cited

U.S. PATENT DOCUMENTS

| | | | |
|---|---|---|---|
| 3,011,922 | 12/1961 | Anderson | 134/1 |
| 3,227,762 | 1/1966 | Brown et al. | 546/13 |
| 4,312,989 | 1/1982 | Spielvogel | 546/13 |
| 4,368,194 | 1/1983 | Spielvogel et al. | 514/64 |

FOREIGN PATENT DOCUMENTS

| | | |
|---|---|---|
| 738333 | 7/1966 | Canada . |
| 0034238 | 8/1981 | European Pat. Off. . |

OTHER PUBLICATIONS

Hall, I. H.: Hypolipidemic Activity of N,N-Dimethyl-n-Octadecyl amine Borane in Rodents, *J. Pharm. Sci.*, 75: (7), 706–710, (1986).

Hall, I. H.: "Hypolipidemic Activity of Boron Analogs in Rodents", Abstr., 36 Southeastern Reg. Meeting, American Chemical Society, Oct. 24–26, 1984, Abst. #332.

Hall, I. H.; Williams, W. L., Gilbert, C. J., McPhail, T. and Spielvogel, B. F., Hypolipidemic Activity of Tetrakis-$\mu$-(Trimethylamine-Borane Carboxylato)-bis(-Trimethylamine-Carboxyborane)-Copper(II) in Rodents and Its Effect on Lipid Metabolism, *J. Pharm. Sci.*, 73(7), 973–977, 1984.

Hall, I. H., Das, M. K., Harchelroad, F., Jr., Wisian–Neilson, P., McPhail, A. T., and Spielvogel, B. F., Antihyperlipidemic Activity of Amine Cyanoboranes, Amine Carboxyboranes, and Related Compounds, *J. Pharm. Sci.*, 70(3), 339–340, 1981.

*Primary Examiner*—Albert T. Meyers
*Assistant Examiner*—Michael S. Wysor
*Attorney, Agent, or Firm*—James R. Thornton

[57] ABSTRACT

Trialkylamine borane compounds are useful as antihyperlipidemic agents for lowering serum cholesterol and triglyceride levels in mammals.

11 Claims, No Drawings

ANTIHYPERLIPIDEMIC AMINE BORANES

This is a continuation-in-part of copending application Ser. No. 785,641 filed on Oct. 8, 1985, now abandoned.

SUMMARY OF THE INVENTION

This invention relates to the use of certain amine borane compounds as antihyperlipidemic or hypolipidemic agents to control mammalian diseases associated with increased serum cholesterol or triglyceride levels.

BACKGROUND OF THE INVENTION

Hall et al., *J. Pharm. Sci.* 70, 339–341 (1981) reported that a series of trimethylamine cyanoboranes and trimethylamine carboxyboranes possess potent hyperlipidemic activity at a dose of 5–20 mg/kg/day. These derivatives lowered serum cholesterol levels, reportedly due to the agents' ability to suppress HMG CoA reductase activity. Reduction of serum triglyceride levels was correlated with the inhibition of fatty acid synthetase by the agents. Subsequently, Hall et al., *J. Pharm. Sci.* 73, 973–977 (1984) reported that tetrakis-$\mu$-(trimethylamine-borane carboxyato)-bis(trimethylamine-carboxyborane)-dicopper (II) was observed to be a potent hypolipidemic agent at the low dose of 2.5 mg/kg in mice. The dicopper complex was observed to lower ATP dependent citrate lyase, acetyl CoA synthetase and phosphatidate phosphohydrolase in vivo and to accelerate cholesterol excretion from the body.

Certain amine borane derivatives which are described as boron analogs of $\alpha$-amino acids have been patented as antiinflammatory agents. See Spielvogel et al. U.S. Pat. No. 4,312,989 issued Jan. 26, 1982.

N,N,N-Trialkylamine boranes are known compounds and have been disclosed to have herbicidal activity. See Canadian Patent No. 738,333 issued July 12, 1966 to Robert F. Crawford.

DESCRIPTION OF THE INVENTION

It has now been found that certain trialkylsubstituted amine borane compounds are potent hypolipidemic agents which do not have the level of toxicity associated with the previously disclosed boron derivatives which possess similar activity.

The amine boranes of the present invention have the formula:

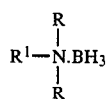

in which each R represents a lower alkyl group of 1 to 4 carbon atoms and $R^1$ represents a higher alkyl group having 4 to about 20 carbon atoms. The $R^1$ group may also be substituted such as by a phenyl group.

Typical examples of groups represented by R include methyl, ethyl, propyl and butyl. Examples of groups represented by $R^1$ include n-butyl, n-hexyl, n-pentyl, n-octyl, 2-ethylhexyl, dodecyl, decyl, tridecyl, hexadecyl, octadecyl, eicosyl, benzyl, and the like. The compounds are normally high-boiling liquids or low-melting crystalline solids which are soluble in the usual organic solvents, such as alcohols and hydrocarbons.

The amine boranes of this invention are readily prepared, such as by the transamination of a tri-lower alkylamine borane, such as triethylamine borane, with the appropriate N-alkyl-N,N-di-lower alkylamine. The reaction proceeds smoothly at elevated temperatures sufficient to remove the tri-lower alkylamine by-product as it is formed. Thus, the preferred reaction temperatures will depend upon the boiling point of the by-product trialkylamine, but generally a temperature in the range of from about 45° to 180° C. is preferred. Solvents or other inert reaction media are not necessary, although, if desired, can be used for close control of the reaction temperature. The desired product is obtained as a reaction residue and can be purified by conventional procedures, such as recrystallization or distillation under reduced pressure.

The following examples are presented to illustrate the preparation of representative compounds of this invention, but it is to be understood that the invention is not to be limited to the specific examples given.

EXAMPLE I

N-n-Octadecyl-N,N-Dimethylamine Borane

To a one-neck round-bottom flask (with thermometer well), equipped with magnetic stirrer, distillation head and condenser, were added 3.87 g. (0.0336 mol) triethylamine borane and 10.0 g. (0.0336 mol) N,N-dimethyloctadecylamine. With stirring, the flask was heated to slowly distill off triethylamine (max. reaction temp. 240° C). After removing 3.2 ml. of triethylamine, heating was interrupted and 10 ml. toluene added to the cooled reaction flask. Distillation was continued until 9.0 ml. were removed (last few drops removed under 15–20 mm. vacuum). The solid in the reaction flask was recrystallized from 30°–60° petroleum ether yielding 7.58 g. (72%) of white crystals, mp 56°–57.5° C. IR (Nujol) 2300 cm$^{-1}$ (B-H). Anal. Calcd for $C_{20}H_{46}BN$: C, 77.14; H, 14.89; B, 3.47; N, 4.50. Found C, 77.21; H, 14.90; B, 3.36; N, 4.50.

EXAMPLE II

N-octyl-N,N-dimethylamine borane

Octyldimethylamine (20.4 grams; 0.130 mole) was heated with triethylamine borane (1.9 grams; 0.130 mole) at reflux temperature until 12.8 grams (98%) of triethylamine had been collected in a cold trap. The reaction residue was distilled at reduced pressure to give N-octyl-N,N-dimethylamine borane boiling at 98°–100° C./0.9 mm. Hg. (19.6 grams; 89% yield).

EXAMPLES III–XIII

The following compounds were prepared by a transamination reaction of triethylamine borane with the appropriate amine as described in the preceding examples.

| Example No. | Compound | M.P. or B.P. |
| --- | --- | --- |
| III | N—nonyl-N,N—dimethylamine borane | liquid |
| IV | N—undecyl-N,N—dimethylamine borane | 23°–23.5° C. |
| V | N—tridecyl-N,N—dimethylamine borane | 38°–39° C. |
| VI | N—pentadecyl-N,N—dimethylamine borane | 49° C. |

-continued

| Example No. | Compound | M.P. or B.P. |
|---|---|---|
| VII | N—tetradecyl-N,N—dimethylamine borane | 36°-39° C. |
| VIII | N—hexadecyl-N,N—dimethylamine borane | 48°-49° C. |
| IX | N—dodecyl-N,N—dimethylamine borane | 31°-32° C. |
| X | N—n-hexyl-N,N—dimethylamine borane | 129.2°-132.9° C./26 mm Hg |
| XI | N—n-butyl-N,N—dimethylamine borane | 100.1°-105.4° C./22 mm Hg |
| XII | N—decyl-N,N—dimethylamine borane | 160.2°-162.2° C./16 mm Hg |
| XIII | N—benzyl-N,N—dimethylamine borane | 98°-100° C. |

The N-alkyl-N,N-di-lower alkylamines can be readily prepared by a Leuckart procedure in which the corresponding alkylamine is reached with formic acid and formaldehyde to give the corresponding N-alkyl-N,N-di-lower alkylamine.

Trialkylamine bornaes are conveniently prepared by reaction of sodium borohydride with the appropriate trialkylamine hydrochloride in the presence of a small amount of water. See Brown et al. U.S. Pat. No. 3,227,762 dated Jan. 4, 1966.

The organo alkylamine boranes of this invention are effective hyperlipidemic agents, being effective both after intraparentoneal and oral administration. They have been found to significantly decrease serum cholesterol and serum triglycerides in mice. When the compounds are employed as hypolipidemic agents, they can be administered to warm-blooded mammals such as mice, rats, rabbits, dogs, cats, monkeys, etc. alone or in combination with pharmacologically acceptable carriers, the proportion of which is determined by the solubility and chemical nature of the compounds, the chosen route of administration and standard biological practice. For example, they may be administered orally in the form of tablets, capsules, lozenges, and the like containing extenders such as starch, milk sugar, etc. They may also be administered orally in the form of solutions or they may be injected parenterally. For parenteral administration they may be used in the form of sterile solutions containing other solutes, for example, enough saline or glucose to make the solution isotonic.

The dosage of the compounds will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in the range of from about 4 mg. to about 20 mg. per kilo per day, although as mentioned above, variations will occur. With the presently preferred compound, N-n-octadecyl-N,N-dimethylamine borane, the optimum dosage appears to be about 8 mg./kg./day in mice and 20 mg./kg. in rats.

The compounds have a relatively low toxicity level. For example, the LD⊖50 of N-n-octadecyl-N,N-dimethylamine borane is over 500 mg./kg. Thus, using the agent at the preferred dosage of 8 mg./kg./day for its hypolipidemic effects is within a safe therapeutic range.

EXAMPLE XIV

For determining hypolipidemic activity, the compounds were suspended in an aqueous 1% carboxymethylcellulose solution and tested at 5 or 20 mg./kg./day administered intraperitoneally to male $CF_1$ mice (~25 g.). On days 9 and 16 blood was collected by tail vein bleeding and the serum separated by centrifugation for three minutes. Serum cholesterol levels were determined by a modified Liebermann-Burchard reaction. Serum triglyceride levels were also determined at 16 days using a Fisher-Hycel Triglyceride Test Kit. The results are presented in Table I.

TABLE I

| | | % of Control | | |
|---|---|---|---|---|
| | Dose | Serum Cholesterol | | Serum Triglyceride |
| Compound | mg./kg. | Day 9 | Day 16 | Day 16 |
| VIII | 20 | 74 | 62 | 72 |
| VII | 20 | 79 | 60 | 102 |
| IV | 5 | 68 | 63 | 82 |
| VI | 20 | 86 | 64 | 70 |
| V | 20 | 88 | 65 | 57 |
| XIII | 20 | 95 | 71 | 60 |
| X | 20 | 66 | 48 | 71 |
| II | 20 | 66 | 69 | 75 |
| XI | 20 | 72 | 62 | 68 |
| XII | 20 | 51 | 46 | 76 |
| IX | 20 | 103 | 97 | 90 |
| I | 20 | 82 | 79 | 77 |
| 1% CMC | | 100 | 100 | 100 |

EXAMPLE XV

The test was repeated at a dosage of 8 mg./kg./day. The results are presented in Table II.

TABLE II

| | | % of Control | | |
|---|---|---|---|---|
| | | Serum Cholesterol | | Serum Triglyceride |
| Compound | Dosage | Day 9 | Day 16 | Day 16 |
| X | 8 mg./kg. | 73 | 69 | 80 |
| II | 8 mg./kg. | 81 | 73 | 74 |
| XI | 8 mg./kg. | 88 | 64 | 72 |
| XII | 8 mg./kg. | 77 | 77 | 79 |
| XIII | 8 mg./kg. | 73 | 65 | 53 |
| VII | 8 mg./kg. | 80 | 67 | 80 |
| IV | 8 mg./kg. | 82 | 68 | 75 |
| IX | 8 mg./kg. | 75 | 74 | 94 |
| V | 8 mg./kg. | 86 | 84 | 76 |
| VI | 8 mg./kg. | 81 | 66 | 77 |
| VIII | 8 mg./kg. | 79 | 59 | 41 |

EXAMPLE XVI

N-n-Octadecyl-N,N-dimethylamine borane was suspended in an aqueous 1% carboxymethylcellulose solution, homogenized, and administered to $CF_1$ male mice (~25 g.) intraperitoneally for 16 days or Sprague Dawley male rats (~350 g.) orally by an intubation needle for 14 days. On days 9 and 14 or 16, blood was obtained by tail vein bleeding and the serum separated by centrifugation for 3 minutes. The serum cholesterol levels were determined by a modification of the Liebermann-Burchard reaction. Serum was also collected on day 14 or 16 and the triglyceride content was determined by a Fisher-Hycel Triglyceride Test Kit. The results are presented in Table III.

The same compound was tested in mice that had been placed on a commercial diet to produce a "hyperlipidemic" state. After the serum cholesterol and triglyceride levels were observed to be elevated, the mice were administered test drugs at 8 mg./kg./day, intraperitoneally for an additional 14-day period. Serum cholesterol and triglyceride levels were measured at that time. A similar lowering of cholesterol and triglyceride levels in the hyperlipidemic-induced mice was observed.

TABLE III

| | Percent of Control (X ± SD) CF$_1$ Mice | | | |
|---|---|---|---|---|
| | Serum Cholesterol | | Serum Triglyceride | |
| N = 6 | Day 9 | Day 16 | Day 9 | Day 16 |
| Control 1% CMC | 100 ± 5$^a$ | 100 ± 6$^b$ | 100 ± 7$^c$ | 100 ± 6$^d$ |
| Treated (Dosage) | | | | |
| 2 mg/kg/day | 71 ± 6* | 61 ± 7* | — | 45 ± 4* |
| 4 mg/kg/day | 69 ± 5* | 59 ± 5* | 80 ± 9 | 49 ± 5* |
| 8 mg/kg/day | 79 ± 7* | 59 ± 4* | 87 ± 7 | 41 ± 3* |
| 12 mg/kg/day | 62 ± 6* | 61 ± 5* | 58 ± 6* | 56 ± 7* |
| 16 mg/kg/day | 60 ± 5* | 61 ± 6* | 73 ± 8* | 63 ± 8* |
| 20 mg/kg/day | 82 ± 7 | 79 ± 7* | — | 77 ± 7* |
| 40 mg/kg/day | 83 ± 6 | 79 ± 8* | — | 93 ± 6 |
| 60 mg/kg/day | 81 ± 6 | 82 ± 6 | — | 113 ± 4 |
| | Sprague Dawley Rats | | | |
| | Serum Cholesterol | | Serum Triglyceride | |
| | Day 9 | Day 14 | Day 9 | Day 14 |
| Control 1% CMC | 100 ± 6$^e$ | 100 ± 6$^f$ | 100 ± 7$^g$ | 100 ± 8$^h$ |
| Treated (Dosage) | | | | |
| 20 mg/kg/day | 82 ± 8 | 46 ± 5* | 82 ± 7 | 65 ± 6* |

*p ≦ 0.001
$^a$118 mg %
$^b$122 mg %
$^c$137 mg %
$^d$141 mg %
$^e$73 mg %
$^f$78 mg %
$^g$110 mg %
$^h$112 mg %

In CF$_1$ male mice the most effective dose of N-n-octadecyl-N,N-dimethylamine borane was 8 mg/kg/day I.P. which reduced serum cholesterol levels 41% and serum triglyceride levels 59%. In Sprague Dawley rats after oral administration at 20 mg/kg/day serum cholesterol levels were reduced 54% and serum triglyceride levels were lowered 35%. In hyperlipidemic induced mice where the serum cholesterol levels has been elevated to 375 mg % from the control value of 128 mg %, 12 days of administering the drug lowered the level to 180 mg %, a 52% reduction. Serum triglyceride levels in the hyperlipidemic mice were elevated to 367 mg/dl compound to the normal value of 137 mg/ dl. Drug treatment for 12 days lowered the hypotriglycemic levels to 187 mg %, a 49% reduction.

In enzymatic studies, it was found that N-n-octadecyl-N, N-dimethylamine borane effectively reduces the liver mitochondrial citrate exchange, ATP dependent citrate lyase and acetyl CoA synthetase activities more than 50% at all concentrations tested in vitro. Cholesterol synthesis (HMG CoA reductase) was reduced in a concentration dependent manner with 200 μM resulting in 38% reduction. Cholesterol 7α hydrolase activity was unaffected by the presence of drugs; however, acyl CoA cholesterol acyl transferase activity was reduced at 100 μM by 41% and at 200 μM by 55%. Actyl CoA carboxylase, fatty acid synthetase and sn-glycerol-3 phosphate acyl transferase activities were unaffected by the drug in vitro. The regulator enzyme, phosphatidate phosphohydrolase, was reduced by the drug with a 67% reduction in activity at 200 μM. Hepatic lipoprotein lipase activity, which was induced by heparin, was reduced 23% at 100 μM and 200 μM concentrations. In vivo N-n-octadecyl-N,N-dimethylamine borane reduced acetyl CoA synthetase 32% at 16 mg/kg/day. ATP dependent citrate lyase activity was reduced 62% at 16 mg/kg/day; HMG CoA reductase activity was reduced maximumly at 4 mg/kg/day by 34%. Cholesterol 7α hydroxylase activity was reduced 35% at 16 mg/kg and acyl CoA cholesterol acyl transferase activity was lowered 52% at 8 mg/kg/day. sn-Glycerol-3-phosphate acyl transferase and phosphatidate phosphohydrolase activities were only moderately reduced at 16 mg/kg/day by 33% and 40%, respectively.

Various changes and modifications of the invention can be made, and to the extent that such variations incorporate the spirit of this invention, they are intended to be included within the scope of the appended claims.

What is claimed is:

1. The method of controlling hyperlipidemia in mammals which comprises administering to said mammal an effective amount of an amine borane of the formula

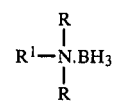

in which
R represents a lower alkyl of 1 to 4 carbon atoms, and
R$^1$ represents a higher alkyl group having 4 to about 20 carbon atoms.

2. The method according to claim 1 in which said amine borane is N-n-octadecyl-N,N-dimethylamine borane.

3. The method according to claim 1 in which said amine borane is N-n-hexyl-N,N-dimethylamine borane.

4. The method according to claim 1 in which said amine borane is N-benzyl-N,N-dimethylamine borane.

5. The method according to claim 1 in which both R groups represent methyl.

6. The method according to claim 1 in which said amine borane is administered at a dosage of from about 4 to about 20 mg./kg./day.

7. The method according to claim 2 in which said amine borane is administered at a dosage of about 8 mg./kg./day.

8. The method according to claim 1 in which said amine borane is N-octyl-N,N-dimethylamine borane.

9. The method according to claim 1 in which said amine borane is N-n-butyl-N,N-dimethylamine borane.

10. The method according to claim 1 in which said amine borane is N-decyl-N,N-dimethylamine borane.

11. The method according to claim 1 in which said amine borane is N-tridecyl-N,N-dimethylamine borane.

* * * * *